United States Patent [19]

Cummins et al.

[11] Patent Number: 5,500,448
[45] Date of Patent: Mar. 19, 1996

[54] RECURRENT APHTHOUS ULCER TREATMENT METHOD

[75] Inventors: Diane Cummins, West Kirby; Franciscus J. Van Der Ouderaa, Neston; Michael D. Traudt, Spital, all of Great Britain

[73] Assignee: Chesebrough-Pond's USA Co., Division of Conopoco, Inc., Greenwich, Conn.

[21] Appl. No.: 241,827

[22] Filed: May 12, 1994

[30] Foreign Application Priority Data

May 13, 1993 [EP] European Pat. Off. ............. 93303712

[51] Int. Cl.$^6$ ...................... A61K 31/075; A61K 31/05; A61K 33/30; A61K 31/315
[52] U.S. Cl. ......................... 514/717; 424/49; 424/641; 424/642; 424/643; 514/900; 514/902; 514/925; 514/928
[58] Field of Search ................................. 514/717, 900, 514/902, 925, 928; 424/49, 641, 642, 643

[56] References Cited

U.S. PATENT DOCUMENTS

| | | | |
|---|---|---|---|
| 4,022,880 | 5/1977 | Vinson et al. | |
| 4,735,802 | 4/1988 | Le | 424/154 |
| 5,188,820 | 2/1993 | Cummins et al. | 424/49 |
| 5,240,696 | 8/1993 | Van Der Ouderaa et al. | |
| 5,286,492 | 2/1994 | Dettmar et al. | 424/458 |
| 5,294,433 | 3/1994 | Singer et al. | 424/52 |

FOREIGN PATENT DOCUMENTS

| | | |
|---|---|---|
| 0455475 | 11/1991 | European Pat. Off. . |
| 0528468 | 2/1993 | European Pat. Off. . |
| 2207604 | 2/1989 | United Kingdom . |
| 93/25209 | 12/1993 | WIPO . |

OTHER PUBLICATIONS

Gilbert et al. J. Dent. Res. 68: 1706–1707 (Nov. 1989) Delivery of Zinc and Trichlosan to Microreservoirs of Antibacterian Derivity.

Ball et al. CA 89: 2042647 U.S. Pat. No. 4,098,877 (Jul. 4, 1978).

Cury et al. Rev. Microbiol. 20/4:490–494 (1989) EMBASE 90283380.

Regoes et al. Dermatologica 158(1):72–79 (1979) as abstracted C.A. 91:747.

Kingston et al. JHYG. (London) 96(2): 185–198 (Apr. 1986) Medline 86197670.

Van Der Hoeven et al. Caries Res. 27(4):298–302 (Apr. 1993) as abstract of GA.120:45736.

Jones et al. J. Dent. Res. 67(1):46–56 (1988) as abstract of GA 108:101097.

Bradshaw et al. J. Dent. Res. 72(1):25–38 (Jan. 1993) as abstract of GA. 118:160617.

Stedman's Medical Dictionary 24th Ed (1982) p. 96 p. 1344—Stomatitis (21 Different Types Defined).

Aphthae—usually caused by a virus or fungus but may occur after Braud Spectrum Antibiotic used enterically chronic intermittent recurrent Aphthae—Reccurrent Scarring Aphthae—Beonar's Aphthae—Ulcerated Palate Newborn Aphthae—Aphthosis—Aphthous—Mikulicz' Aphthae.

PCT Search Report PCT/EP 94/10288 Krautbauer 30 Aug. 1994.

PCT Application WO 92/10994 9 Jul. 1992 Cox et al. (Procter & Gamble).

PCT Application WO 93/02717 18 Feb. 1993 Richardson (Smith & Nephew).

Minerva Stomatol (Italy)—Jul.–Sep. 1979, vol. 28, No. 3, pp. 209–214. Piccione.

Int. J. Cosmet. Sci. (United Kingdom)—1991, vol. 13, No., pp. 29–42 Verran.

(Regression of Aphthae with chlorohexide glucorate would work on covitols) Triclosan and Zinc Citrate Syner–sinually reduces plaque Candida Albicans causes Stomatis—Treatment Involves Plaque Removal and Antifungals and Antiseptics.

*Primary Examiner*—Shep K. Rose
*Attorney, Agent, or Firm*—Milton L. Honig

[57] ABSTRACT

The present invention relates to the use of Triclosan in the manufacture of a composition for the prevention, inhibition and/or reduction of aphthous ulcers. Preferably, the compositions are oral compostions such as toothpastes and mouthwashes. The oral composition is especially preferably in a gel form. Preferably the Triclosan is used together with a zinc salt such as zinc citrate, and or a polymer that enhances the delivery of the Triclosan.

6 Claims, No Drawings

RECURRENT APHTHOUS ULCER TREATMENT METHOD

BACKGROUND OF THE INVENTION

Field of the Invention

The present invention relates to the prevention, inhibition and/or reduction of minor recurrent aphthous stomatitis by the use of an oral composition which comprises Triclosan (= 2',4,4'-trichloro-2-hydroxy-diphenyl-ether).

The Related Art

Aphthous stomatitis is a general term describing a disease affecting the mucous membrane in the mouth, causing the formation of small, whitish ulcers, called aphthae or more commonly aphthous ulcers. These aphthous ulcers cause severe discomfort to the patient as they are rather painful and irritating. Several treatments for aphthous ulcers have already been proposed, e.g. gargle compositions with an astringent material or with cellulose alkyl ethers or with homocarnosine, but none of these treatments have found wide usage as effective anti-aphthae treatments.

SUMMARY OF THE INVENTION

We have now found that Triclosan has a considerable anti-aphthae activity, significantly preventing, inhibiting and/or reducing the formation of aphthous ulcers in the mouth.

Consequently, the present invention relates to the use of Triclosan in the manufacture of composition for preventing inhibiting and/or reducing aphthous ulcers.

Triclosan is a well-known anti-bacterial agent, used in oral compositions to reduce or inhibit the growth of dental plaque. Its use to prevent, inhibit and/or reduce aphthous ulcers has not been indicated in the prior art as far as we know.

The Triclosan-containing composition of the present invention can be manufactured in any form, suitable for orally administering the composition to achieve the prevention, inhibition and/or reduction of aphthous ulcers. Such forms are tablets, capsules, pills, powders, granules, solutions, gargles, suspensions, salves, gels, pastes etc. Preferably, the composition is an oral composition. Particularly suitable forms of the oral composition are toothpastes, mouthwashes, gels and the like. Also it is possible to formulate the oral composition in forms, suitable for buccal administration, such as irrigator fluids, chewing gum, lozenges, and adhesive strips. Oral compositions in gel form are particularly preferred in the present invention.

DETAILED DESCRIPTION

The amount of Triclosan used in the present invention may vary from 0.0001–5% by weight, preferably from 0.01–3% by weight and particularly preferably from 0.1–2% by weight of the oral composition.

The oral composition may furthermore comprise, conventional ingredients, such as pharmaceutically acceptable carriers like starch, sucrose, polyols, surfactants, water or water/alcohol systems etc. When formulated into a dentifrice, such formulation may contain all the usual dentifrice ingredients. Thus, they may comprise particulate abrasive materials such as silicas, aluminas, calcium carbonates, dicalciumphosphates, hydroxyapatites, trimetaphosphates, insoluble hexametaphosphates and so on, usually in amounts between 5 and 60% by weight.

Furthermore, the dentifrice formulations may comprise humectants such as glycerol, sorbitol, propyleneglycol, lactitol and so on.

Surface-active agents may also be included such as anionic, nonionic, amphoteric and zwitterionic synthetic detergents. Examples thereof are sodiumlaurylsulphate, sodium dodecylbenzenesulphonate, sodium mono- and dioctylphosphate, sodiumlauroylsarcosinate.

Binders and thickeners such as sodium carboxymethylcellulose, xanthan gum, gum arabic etc. may also be included, as well as synthetic polymers such as polyacrylates and carboxyvinyl polymers such as Carbopol®.

Flavours such as peppermint and spearmint oils may also be included, as well as preservatives, opacifying agents, colouring agents, pH-adjusting agents, sweetening agents and so on.

Other anti-bacterial agents may also be included such as chlorhexidine, copper-, zinc- and stannous salts such as zinc citrate and stannous pyrophosphate, sanguinarine extract, metronidazole. Further examples of anti-bacterial agents are quaternary ammonium compounds such as cetylpyridinium chloride; bis-guanides such as chlorhexidine digluconate, hexetidine, octenidine, alexidine; halogenated bisphenolic compounds such as 2,2'-methylenebis-(4-chloro-6-bromophenol).

Polymeric compounds which can enhance the delivery of active ingredients such as the anti-bacterial agents can also be included. Examples of such polymers are copolymers of polyvinylmethylether with maleic anhydride and other similar delivery enhancing polymers, e.g. those described in DE-A-3,942,643 (Colgate).

Furthermore anti-inflammatory agents such as ibuprofen, flurbiprofen, aspirin, indomethacin etc. may also be included.

Anti-caries agents such as sodium- and stannous fluoride, aminefluorides, monosodiumfluorophosphate, calcium lactate and/or calcium glycerophosphates, strontium salts and strontium polyacrylates, casein and casein digests and phosphoproteins may also be included.

Other optional ingredients include vitamins such as Vitamin C, plant extracts, potassium salts such as potassium citrate, potassium chloride and potassium nitrate.

Other optional ingredients include enzymes such as dextranase and/or mutanase, amyloglucosidase, glucoseoxidase with lactoperoxidase, neuraminidases, and hydrogenperoxide generating compounds such as potassiumperoxydiphosphate.

Furthermore, the oral compositions may comprise anticalculus agents such as alkalimetalpyrophosphates, hypophosphite-containing polymers, organic phosphonates, phosphocitrates etc.

Other optional ingredients that may be included are e.g. bacteriocins, bacteriophages, tissue respiratory factors, antibodies, bleaching agents such as peroxy compounds, effervescing systems such as sodiumbicarbonate/citric acid systems, colour change systems, and so on.

Preferred compositions for use in the present invention contain Triclosan together with a zinc salt such as zinc citrate. The amount of zinc salt used in such combination ranges from 0.01–5% by weight of the composition, preferably from 0.1–3% by weight of the composition. Other suitable zinc salts are those, disclosed in U.S. Pat. No. 4,022,880, as well as alkalimetal zinc citrates such as sodium zinc citrate.

Also preferred for use in the present invention are compositions which contain Triclosan and a copolymer of polyvinylmethylether with maleic anhydride or another delivery-enhancing polymer as described in DE-A-3,942,643. The amount of such polymer may vary from 0.005-4% by weight of the composition. A zinc salt may also be present in these polymer-containing compositions, such as zinc citrate or zinc glycinate in the above specified amounts.

The invention will further be illustrated by the following Examples:

EXAMPLE 1

The following formulation is a toothpaste formulation that reduces aphthous ulcers:

|  | wt % |
|---|---|
| Sorbitol, 70% syrup | 45.00 |
| Abrasive silica | 10.00 |
| Thickening silica | 10.00 |
| Xanthan gum | 1.00 |
| Saccharin | 0.20 |
| Titanium dioxide | 1.00 |
| Sodium monofluorophosphate | 0.80 |
| Flavour | 1.00 |
| Polyethylene glycol | 5.00 |
| Zinc citrate.3H$_2$O | 0.75 |
| Triclosan | 0.30 |
| Water | q.s. |

EXAMPLE 2

The following compositions are mouthwash formulations that reduce aphthous ulcers:

| Ingredients | % by weight | |
|---|---|---|
| Glycerol (85% w/w) | — | — |
| Propylene glycol | — | — |
| Glycine | 1.00 | 0.50 |
| Sodium fluoride | 0.02 | 0.02 |
| Sorbitol syrup (70% w/w) | 40.00 | 20.00 |
| ethanol | 15.60 | 7.80 |
| Nonionic block copolymer surfactant | 1.00 | 0.50 |
| Sodium hydroxide | 1.08 | 0.74 |
| Sodium lauryl sulphate | — | 0.10 |
| Saccharin | — | — |
| ethoxylated hydrogenated castor oil | — | — |
| Flavour | 0.20 | 0.15 |
| Zinc sulphate heptahydrate | 0.40 | 0.40 |
| Triclosan | 0.15 | 0.15 |
| Blue Dye | 0.03 | 0.03 |
| Water | q.s | q.s. |

What is claimed is:

1. A method for reducing and/or inhibiting and/or preventing recurrent aphthous ulcers in an afflicted patient, comprising applying Triclosan to said ulcers.

2. A method according to claim 1 wherein said Triclosan is delivered in an oral composition.

3. A method according to claim 2 wherein said oral composition is selected from the group consisting of dentifrices and mouthwashes.

4. A method according to claim 2 wherein the oral composition is in a gel form.

5. A method according to claim 1, further comprising applying to said ulcers a zinc salt in combination with said Triclosan.

6. A method according to claim 2 wherein said oral composition further comprises a polymer to enhance delivery of said Triclosan.

\* \* \* \* \*

UNITED STATES PATENT AND TRADEMARK OFFICE
CERTIFICATE OF CORRECTION

PATENT NO. : 5,500,448
DATED      : March 19, 1996
INVENTOR(S): Cummins et al.

It is certified that error appears in the above-indentified patent and that said Letters Patent is hereby corrected as shown below:

On the title page, item [73],

Please change "Conopoco, Inc." to read -- Conopco, Inc. -- .

Signed and Sealed this

Sixteenth Day of July, 1996

*Attest:*

BRUCE LEHMAN

*Attesting Officer*        *Commissioner of Patents and Trademarks*